United States Patent [19]
Bower et al.

[11] Patent Number: 6,017,870
[45] Date of Patent: Jan. 25, 2000

[54] PURIFIED CELLULASE AND METHOD OF PRODUCING

[75] Inventors: Benjamin S. Bower, Pacifica; Kathleen A. Clarkson, San Francisco; Katherine D. Collier, Redwood City; James T. Kellis, Portola Valley; Moira B. Kelly, San Francisco; Edmund A. Larenas, Moss Beach, all of Calif.

[73] Assignee: Genencor International, Inc., Rochester, N.Y.

[21] Appl. No.: 08/728,350

[22] Filed: Oct. 9, 1996

[51] Int. Cl.[7] .............................. C11D 3/386; C12N 9/42; A23K 1/165
[52] U.S. Cl. ..................... 510/392; 510/393; 510/530; 8/116.1; 8/401; 435/209; 435/69.1; 426/630; 162/70
[58] Field of Search ................................. 510/392, 393, 510/530; 8/116.1, 401; 435/209, 69.1; 424/630; 162/70

[56] References Cited

U.S. PATENT DOCUMENTS

| | | | |
|---|---|---|---|
| 5,290,474 | 3/1994 | Clarkson et al. | 252/174.12 |
| 5,472,864 | 12/1995 | Bower | 435/209 |
| 5,475,101 | 12/1995 | Ward et al. | 536/23.74 |
| 5,703,037 | 12/1997 | Bae-Lee | 510/320 |
| 5,707,858 | 1/1998 | Screws et al. | 435/263 |
| 5,753,483 | 5/1998 | Ward et al. | 435/209 |
| 5,856,165 | 1/1999 | Van Solingen | 435/209 |
| 5,866,392 | 2/1999 | Schou et al. | 435/190 |
| 5,912,157 | 6/1999 | von der Oslen et al. | 435/209 |

FOREIGN PATENT DOCUMENTS

| | | | |
|---|---|---|---|
| WO 88/08855 | 11/1988 | WIPO | C08B 30/04 |
| WO 94/07983 | 4/1994 | WIPO | C11D 3/386 |
| WO 95/16360 | 6/1995 | WIPO | A23K 1/165 |

OTHER PUBLICATIONS

Hong, Jeong–Hwa, "Cross–synergistic interactions between *Trichoderma viride* and *Penicillium funiculosum* cellulase," *Journal of the Korean Society of Food and Nutrition*, V 22, No. 3, pp. 340–348, (1993).

Luderer, M.E.H. et al., "A re–appraisal of multiplicity of enoglucanase I from *Trichoderma reesei* using monclonal antibodies and plasma desorption mass spectrometry," *Biochimica et Biophysica Acta*, V 1076, No. 3, pp.427–434(1991).

Saloheimo, M. et al., "cDNA cloning of a *Trichoderma reesei* cellulase and demonstration of endoglucanase activity by expression in yeast," *European Journal of Biochemistry*, V. 249, 1997, Berlin DE pp. 584–591.

*Primary Examiner*—Kery Fries
*Attorney, Agent, or Firm*—Christopher L. Stone; Genencor International, Inc.

[57] ABSTRACT

A purified novel cellulase composition is provided which may be isolated from a fermentation culture of *Trichoderma longibrachiatum* and has a molecular weight of about 95–105 kD as approximated on SDS-PAGE (see FIG. 1), a pI of about 5.6–6.8 as estimated on an IEF gel and a pH optimum of about 5.0 on RBB-CMC when measured at 65° C. and pH 4 or lower at temperatures of 40° C. and 50° C.

19 Claims, 3 Drawing Sheets

PURIFIED CELLULASE AND METHOD OF PRODUCING

BACKGROUND OF THE INVENTION

1. Field of the Invention

The present invention is directed to purified or isolated cellulase corresponding to EGVI from Trichoderma spp. The present invention further relates to methods of isolating purified EG VI cellulase obtained from Trichoderma spp. or genetically modified strains of Trichoderma spp. and to methods for using that cellulase in detergents, textile treatment, improving the value of animal feed, processing pulp and paper, grain wet milling and other methods for using cellulase which are known in the art.

2. State of the Art

Cellulases are enzymes which are capable of the hydrolysis of the β-D-glucosidic linkages in celluloses. Cellulolytic enzymes have been traditionally divided into three major classes: endoglucanases, exoglucanases or cellobiohydrolases and β-glucosidases (Knowles, J. et al. (1987), TIBTECH 5, 255–261); and are known to be produced by a large number of bacteria, yeasts and fungi.

Primary among the applications that have been developed for the use of cellulolytic enzymes are those involving degrading (wood)cellulose pulp into sugars for (bio)ethanol production, textile treatments like 'stone washing' and 'biopolishing', and in detergent compositions. Thus, cellulases are known to be useful in the treatment of mechanical pulp (see e.g., PCT Publication No. WO 92/16687). Additionally, cellulases are known to be useful as a feed additive (see e.g., PCT Publication No. WO 91/04673) and in grain wet milling.

Of primary importance, however, cellulases are used in the treatment of textiles, i.e., in detergent compositions for assisting in the removal of dirt or grayish cast (see e.g., Great Britain Application Nos. 2,075,028, 2,095,275 and 2,094,826 which illustrate improved cleaning performance when detergents incorporate cellulase) or in the treatment of textiles prior to sale, i.e., for improving the feel and appearance of the textile. Thus, Great Britain Application No. 1,358,599 illustrates the use of cellulase in detergents to reduce the harshness of cotton containing fabrics and cellulases are used in the treatment of textiles to recondition used fabrics by making their colors more vibrant (see e.g., The Shizuoka Prefectural Hammamatsu Textile Industrial Research Institute Report, vol. 24, pp. 54–61 (1986). For example, repeated washing of cotton containing fabrics results in a greyish cast to the fabric which is believed to be due to disrupted and disordered fibrils, sometimes called "pills", caused by mechanical action. This greyish cast is particularly noticeable on colored fabrics. As a consequence, the ability of cellulase to remove the disordered top layer of the fiber and thus improve the overall appearance of the fabric has been of value.

While cellulases are produced (expressed) in fungi, bacteria and the like, cellulase produced by certain fungi, and in particular by the fungal genus Trichoderma spp. (especially *Trichoderma longibrachiatum*), have been given much attention because a complete cellulase system capable of degrading crystalline forms of cellulose is readily produced in large quantities via fermentation procedures.

Wood et al, "Methods in Enzymology", 160, 25, pages 234 et seq. (1988), disclose that complete fungal cellulase systems comprise several different enzyme classifications including those identified as exo-cellobiohydrolases (EC 3.2.1.91) ("CBH"), endoglucanases (EC 3.2.1.4) ("EG"), and β-glucosidases (EC 3.2.1.21) ("BG"). The fungal cellulase classifications of CBH, EG and BG can be further expanded to include multiple components within each classification. CBHs and EGs have been isolated from a variety of fungal sources. U.S. Pat. No. 5,475,101 (Ward et al.) discloses the purification and molecular cloning of EGIII from *Trichoderma longibrachiatum*. PCT Publication No. 94/28117 discloses the isolation and sequence of a 20–25 kD cellulase derived from *Trichoderma reesei* called EGV.

Despite knowledge in the art related to many cellulase compositions having some or all of the above properties, there is a continued need for new cellulases having a varying spectrum of characteristics which are useful in, for example, treating textiles, as a component of detergent compositions, in the treatment of pulp and paper, and in the conversion of biomass. Applicants have discovered a new cellulase isolated from a fermentation broth of *Trichoderma longibrachiatum* which has heretofore been unknown in the art.

SUMMARY OF THE INVENTION

It is an object of the present invention to provide for a new cellulase having a novel complement of characteristics which are useful in industrial processes which utilize cellulase, e.g., detergents, textile treatment, as an animal feed additive, in grain wet milling, and in the processing of pulp and paper.

According to the present invention, a purified novel cellulase composition is provided which substantially corresponds to EGVI as defined herein. EGVI may be isolated from a fermentation culture of *Trichoderma longibrachiatum* and has a molecular weight of about 95–105 kD as approximated on SDS-PAGE (see FIG. 1), a pI of about 5.6–6.8 as estimated on an IEF gel and a pH optimum of about 5.0 on RBB-CMC when measured at 65° C. and pH 4 or lower at temperatures of 40° C. and 50° C.

According to a process embodiment of the present invention, a method is provided for purifying or isolating a cellulase corresponding to EGVI from a fermentation culture of Trichoderma sp. Preferably, the fermentation culture comprises *Trichoderma longibrachiatum*. Further preferably, the strain of *Trichoderma longibrachiatum* has been genetically modified so as to be deleted for cellulases CBHI, CBHII, EGI, EGII, EGIII and EGV, for example, according to the teachings of U.S. Pat. No. 5,328,841.

The instant invention further contemplates a method of treating cellulose containing fabric comprising contacting the cellulose containing fabric with the purified cellulase according to the invention. In a process embodiment of the invention, the result of the method is to produce a stonewashed effect or an improvement in the feel and/or appearance of the fabric. In an alternative process embodiment of the invention, the cellulose containing fabric is contacted with an aqueous solution containing a detergent composition comprising the purified cellulase according to the invention. In yet another process embodiment of the invention, the purified cellulase of the invention is used to treat cellulosic material comprising wood or paper pulp and the addition of cellulase facilitates the production of paper products therefrom. In yet another process embodiment of the invention, the purified cellulase of the invention is used as an additive to treat a cellulosic material comprising animal feed and the method results in an increase in the digestibility or nutritive value of said animal feed.

The invention, along with its objects and advantages, will be described in more detail below.

DETAILED DESCRIPTION OF THE INVENTION

Figure 1:
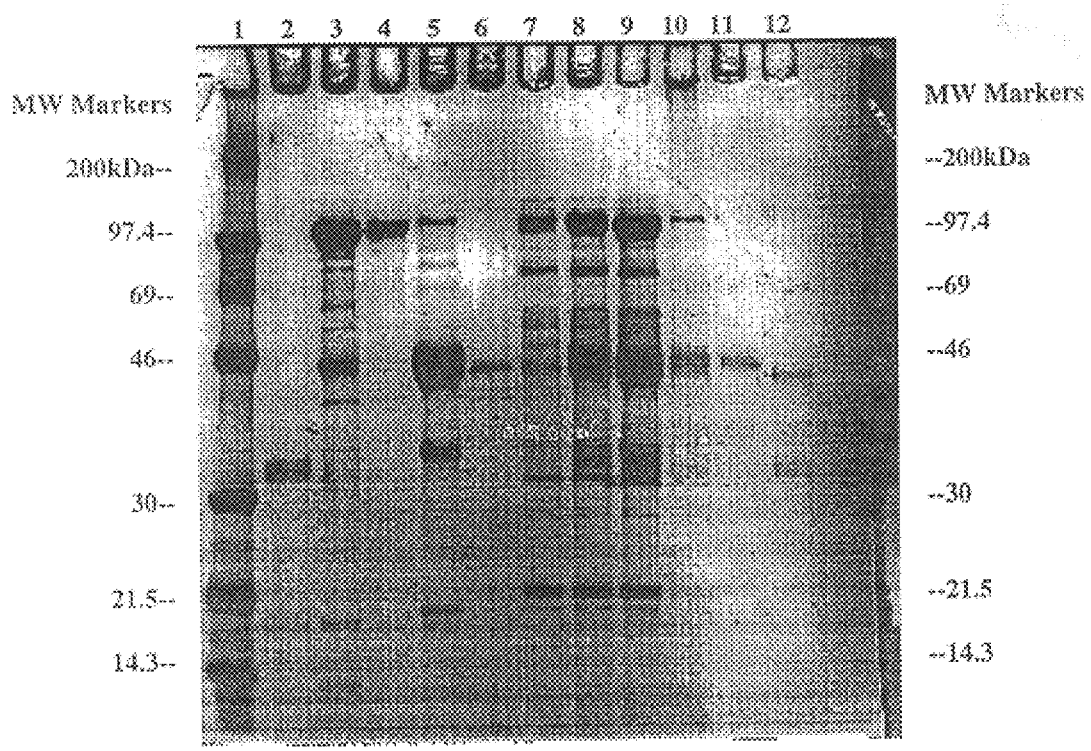
FIG. 1 illustrates an SDS-PAGE gel showing the comparative molecular weight of EGVI with other known protein markers. Purified EGVI was loaded in lane 4 with marker molecular weights shown in the margin.

"Cotton-containing fabric" means sewn or unsewn garments, yarns or fibers made of pure cotton or cotton blends including cotton woven fabrics, cotton knits, cotton denims, cotton yarns and the like. When cotton blends are employed, the amount of cotton in the fabric is preferably at least about 35 percent by weight cotton. When employed as blends, the companion material employed in the fabric can include one or more non-cotton fibers including synthetic fibers such as polyamide fibers (for example, nylon 6 and nylon 66), acrylic fibers (for example, polyacrylonitrile fibers), and polyester fibers (for example, polyethylene terephthalate), polyvinyl alcohol fibers (for example, Vinylon), polyvinyl chloride fibers, polyvinylidene chloride fibers, polyurethane fibers, polyurea fibers and aramid fibers.

"Cellulose containing fabric" means any sewn or unsewn garments, yarns or fibers which contain cotton or non-cotton containing cellulose or cotton or non-cotton containing cellulose blends including natural cellulosics and manmade cellulosics (such as jute, flax, ramie, rayon, and lyocell). Included under the heading of manmade cellulose containing fabrics are regenerated fabrics that are well known in the art such as rayon. Other manmade cellulose containing fabrics include chemically modified cellulose fibers (e.g, cellulose derivatized by acetate) and solvent-spun cellulose fibers (e.g. lyocell). Specifically included within the definition of cellulose containing fabric is any yarn or fiber made of such materials.

"Stonewashing composition" means a formulation for use in stonewashing cellulose containing fabrics. Stonewashing compositions are used to modify cellulose containing fabrics prior to presentation for consumer sale, i.e., during the manufacturing process. In contrast, detergent compositions are intended for the cleaning of soiled garments.

"Stonewashing" means the treatment of cellulose containing fabric with a cellulase solution under agitating and cascading conditions, i.e., in a rotary drum washing machine, to impart a "stonewashed" appearance to the denim. The cellulase solution according to the instant invention will functionally replace the use of stones in such art recognized methods, either completely or partially. Methods for imparting a stonewashed appearance to denim are described in U.S. Pat. No. 4,832,864 which is incorporated herein by reference in its entirety. Generally, stonewashing techniques have been applied to indigo dyed denim.

"Detergent composition" means a mixture which is intended for use in a wash medium for the laundering of soiled cellulose containing fabrics. In the context of the present invention, such compositions may include, in addition to cellulases and surfactants, additional hydrolytic enzymes, builders, bleaching agents, bleach activators, bluing agents and fluorescent dyes, caking inhibitors, masking agents, cellulase activators, antioxidants, and solubilizers may be included. Such compositions are generally used for cleaning soiled garments and are not used during the manufacturing process, in contrast to stonewashing compositions. Detergent compositions comprising cellulase are described in, for example, Clarkson et al., U.S. Pat. No. 5,290,474 and EP Publication No. 271 004, incorporated herein by reference.

According to the present invention, a novel purified cellulase composition is provided which substantially corresponds to EGVI as defined herein. EGVI is a cellulase produced during a fermentation culture of *Trichoderma longibrachiatum* having a molecular weight of about 95–105 kD (approximately 100 kD) as approximated on SDS-PAGE (see FIG. 1), a pI of about 5.6–6.8 (approximately 6.2) as estimated on an IEF gel and a pH optimum of about 5.0 on RBB-CMC when measured at 65° C. and pH 4 or lower at temperatures of 40° C. and 50° C. EGVI also appears to have cellulase binding activity.

According to a process embodiment of the present invention, a method is provided for purifying or isolating a cellulase substantially corresponding to EGVI from a fermentation culture of Trichoderma sp. Preferably, the fermentation culture comprises *Trichoderma longibrachiatum*. Further preferably, the strain of *Trichoderma longibrachiatum* has been genetically modified so as to be deleted for cellulases CBHI, CBHII, EGI, EGII, EGIII and EGV according to the teachings of U.S. Pat. No. 5,328,841.

In the context of the present invention, the inventive purified cellulase corresponds to a naturally occurring cellulase produced during a fermentation culture of *Trichoderma longibrachiatum* having a molecular weight of about 95–105 kD (approximately 100 kD) as measured on SDS-PAGE, a pI of about 5.6–6.8 (approximately 6.2) as estimated on an IEF gel. Thus, the purified cellulase, as defined herein, may be produced by any microorganism which is capable of producing a similar cellulase. The purified cellulase of the present invention is purified in the sense that it is present in partially or fully isolated form at a concentration different from that found in a fermentation of naturally occurring or otherwise known strains of *Trichoderma longibrachiatum* or in combination with constituents not normally associated with such fermentation broths. It is conceived that a genetically engineered microorganism may be transformed with DNA encoding the cellulase according to the invention and subsequently grown under suitable fermentation conditions to induce production of the cellulase. Similarly, it is conceived that the purified cellulase according to the invention may be produced in substantially homologous form by a different organism than *Trichoderma longibrachiatum* from which Applicants first isolated EGVI. Particularly, it is conceived that fungi, including filamentous fungus and specifically including Trichoderma spp., e.g., *Trichoderma viride,* may produce cellulases which exhibit substantial identity with EGVI. By substantial identity is meant that a cellulase may show substantially identical properties in terms of molecular weight, isoelectric point, pH profile and/or temperature profile. Such cellulases exhibiting substantial identity are considered herein to "correspond" to EGVI. Similarly, it is conceived that it may be possible to modify the cellulase according to the invention to have slightly different properties by, for example, random mutagenesis of the producing organism, site specific mutagenesis of the gene encoding the cellulase according to the invention and/or chemical alteration of the enzyme after expression or secretion.

In general, compositions comprising the purified cellulase according to the invention can be obtained by purification techniques based on the identified characteristics and properties of the cellulase according to the invention. Specifically, where the purified cellulase according to the invention is part of a mixture of cellulases produced by the cultured organism, the entire cellulase mixture (whole cellulase) can be purified into substantially pure components by recognized separation techniques published in the literature, including ion exchange chromatography at a suitable pH, affinity chromatography, size exclusion and the like. For example, in ion exchange chromatography (i.e., anion or cation exchange chromatography), it is possible to separate the cellulase components by eluting with a pH gradient, or a salt gradient, or both a pH and a salt gradient. After purification, the requisite amount of the desired components could be recombined. Alternatively, genetic engineering techniques may be used to manipulate the produced cellulase mixtures, for example through the use of strains deleted in cellulase genes wherein the gene encoding the cellulase according to the invention is transformed and/or expressed by the otherwise cellulase deleted host strain.

Treatment of textiles according to the present invention contemplates textile processing or cleaning with a composition comprising a cellulase which may be used in treating a cellulose containing fabric. Such treatment includes, but is not limited to, stonewashing, modifying the texture, feel and/or appearance of cellulose containing fabrics or other techniques used during manufacturing or cleaning/reconditioning of cellulose containing fabrics. Additionally, treating within the context of this invention contemplates the removal of "immature" or "dead cotton", from cellulosic fabric or fibers, i.e. immature cotton which is significantly more amorphous than mature cotton. Dead cotton is known to cause uneven dyeing and is undesirable. Accordingly, the composition contemplated in the present invention includes compositions comprising a cellulase component intended for use in washing of a soiled manufactured cellulose containing fabric. For example, cellulase may be used in a detergent composition for washing laundry. Detergent compositions useful in accordance with the present invention include special formulations such as pre-wash, pre-soak and home-use color restoration compositions. Such treating compositions, as described herein, may be in the form of a concentrate which requires dilution or in the form of a dilute solution or form which can be applied directly to the cellulose containing fabric. General treatment techniques known in the art for cellulase treatment of textiles are described in, for example, EP Publication No. 220 016 and GB Application Nos. 1,368,599 and 2,095,275.

Thus, according to a preferred embodiment of the present invention, the cellulase compositions described above may be employed as a stonewashing composition. Preferably, stonewashing according to the instant invention comprises preparing an aqueous solution which contains an effective amount of cellulase together with other optional ingredients including, for example, a buffer, a surfactant, and a scouring agent. An effective amount of cellulase enzyme composition is a concentration of cellulase enzyme sufficient for its intended purpose. Thus an "effective amount" of cellulase in the stonewashing composition according to the present invention is that amount which will provide the desired treatment, e.g., stonewashing. The amount of cellulase employed is also dependent on the equipment employed, the process parameters employed (the temperature of the cellulase treatment solution, the exposure time to the cellulase solution, and the like), and the cellulase activity (e.g., a particular solution will require a lower concentration of cellulase where a more active cellulase composition is used as compared to a less active cellulase composition). The exact concentration of cellulase in the aqueous treatment solution to which the fabric to be stonewashed is added can be readily determined by the skilled artisan based on the above factors as well as the desired result. Preferably the cellulase composition is present in a concentration of from 1 to 5,000 ppm and most preferably 10 to 200 ppm total protein.

Optionally, a buffer is employed in the stonewashing composition such that the concentration of buffer is sufficient to maintain the pH of the solution within the range wherein the employed cellulase exhibits activity which, in turn, depends on the nature of the cellulase employed. The exact concentration of buffer employed will depend on several factors which the skilled artisan can readily take into account. For example, in a preferred embodiment, the buffer as well as the buffer concentration are selected so as to maintain the pH of the final cellulase solution within the pH range required for optimal cellulase activity.

In addition to cellulase and a buffer, the stonewashing composition may optionally contain a surfactant. Suitable surfactants include any surfactant compatible with the cellulase and the fabric including, for example, anionic, nonionic and ampholytic surfactants. Suitable anionic surfactants for use herein include linear or branched alkylbenzenesulfonates; alkyl or alkenyl ether sulfates having linear or branched alkyl groups or alkenyl groups; alkyl or alkenyl sulfates; olefinsulfonates; alkanesulfonates and the like. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3. Ampholytic surfactants include quaternary ammonium salt sulfonates, and betaine-type ampholytic surfactants. Such ampholytic surfactants have both the positive and negative charged groups in the same molecule. Nonionic surfactants generally comprise polyoxyalkylene ethers, as well as higher fatty acid alkanolamides or alkylene oxide adduct thereof, and fatty acid glycerine monoesters. Mixtures of surfactants can also be employed in manners known to those skilled in the art.

In a preferred embodiment, a concentrated stonewashing composition can be prepared for use in the methods described herein. Such concentrates would contain concentrated amounts of the cellulase composition described above, buffer and surfactant, preferably in an aqueous solution. When so formulated, the stonewashing concentrate can readily be diluted with water so as to quickly and accurately prepare stonewashing compositions according to the present invention and having the requisite concentration of these additives. When aqueous concentrates are formulated, these concentrates can be diluted so as to arrive at the requisite concentration of the components in the cellulase solution as indicated above. As is readily apparent, such stonewashing concentrates will permit facile formulation of the cellulase solutions as well as permit feasible transportation of the concentration to the location where it will be used. The stonewashing concentrate can be in any art recognized form, for example, liquid, emulsion, gel, or paste. Such forms are well known to those skilled in the art.

When a solid stonewashing concentrate is employed, the cellulase composition may be a granule, a powder, an agglomerate or a solid disk. When granules are used, the granules are preferably formulated so as to contain a cellulase protecting agent. See, for instance, U.S. Ser. No. 07/642,669, filed Jan. 17, 1991 as Attorney Docket No. 010055-073 and entitled "GRANULES CONTAINING BOTH AN ENZYME AND AN ENZYME PROTECTING AGENT AND DETERGENT COMPOSITIONS CONTAINING SUCH GRANULES," which application is incorporated herein by reference in its entirety. Likewise, the granules can be formulated so as to contain materials to reduce the rate of dissolution of the granules into the wash medium. Such materials and granules are disclosed in U.S. Pat. No. 5,254,283 which is incorporated herein by reference in its entirety.

Other materials can also be used with or placed in the stonewashing composition of the present invention as desired, including stones, pumice, fillers, solvents, enzyme activators, and other anti-redeposition agents.

The cellulose containing fabric is contacted with the stonewashing composition containing an effective amount of the cellulase by intermingling the fabric with the stonewashing composition, and thus bringing the cellulase enzyme into proximity with the fabric. If the stonewashing composition is an aqueous solution, the fabric may be directly soaked in the solution. Similarly, where the stonewashing composition is a concentrate, the concentrate is diluted into a water bath with the cellulose containing fabric. When the stonewashing composition is in a solid form, for example a pre-wash gel or solid stick, the stonewashing composition may be contacted by directly applying the composition to the fabric or to the wash liquor. Subsequently, the aqueous solution containing the cellulase and the fabric is agitated.

The cellulose containing fabric is incubated with the stonewashing composition under conditions effective to allow the enzymatic action to confer a stonewashed appearance to the cellulose containing fabric. For example, during stonewashing, the pH, liquor ratio, temperature and reaction time may be adjusted to optimize the conditions under which the stonewashing composition acts. "Effective conditions" necessarily refers to the pH, liquor ratio, and temperature which allow the cellulase enzyme to react efficiently with cellulose containing fabric. The reaction conditions for cellulase, and thus the conditions effective for the stonewashing compositions of the present invention, are substantially similar to well known methods used with corresponding prior art cellulase compositions. Accordingly, it is within the skill of those in the art to maximize conditions for using the stonewashing compositions according to the present invention.

The liquor ratios during stonewashing, i.e., the ratio of weight of stonewashing composition solution (i.e., the wash liquor) to the weight of fabric, employed herein is generally an amount sufficient to achieve the desired stonewashing effect in the denim fabric and is dependent upon the process used. Preferably, the liquor ratios are from about 4:1 to about 50:1, more preferably from 5:1 to about 20:1, and most preferably from about 10:1 to about 15:1.

Reaction temperatures during stonewashing with the present stonewashing compositions are governed by two competing factors. Firstly, higher temperatures generally correspond to enhanced reaction kinetics, i.e., faster reactions, which permit reduced reaction times as compared to reaction times required-at lower temperatures. Accordingly, reaction temperatures are generally at least about 10° C. and greater. Secondly, cellulase is a protein which loses activity beyond a given reaction temperature which temperature is dependent on the nature of the cellulase used. Thus, if the reaction temperature is permitted to go too high, then the cellulolytic activity is lost as a result of the denaturing of the cellulase.

Reaction times are dependent on the specific conditions under which the stonewashing occurs. For example, pH, temperature and concentration of cellulase will all effect the optimal reaction time. Generally, reaction times are from about 5 minutes to about 5 hours, and preferably from about 10 minutes to about 3 hours and, more preferably, from about 20 minutes to about 1 hour.

According to yet another preferred embodiment of the present invention, the cellulase compositions described above may be employed in a detergent composition. The detergent compositions according to the present invention are useful as pre-wash compositions, pre-soak compositions, or for detergent cleaning during the regular wash cycle. Preferably, the detergent composition of the present invention comprises an effective amount of cellulase, and a surfactant, and optionally includes other ingredients described below.

An effective amount of cellulase employed in the detergent compositions of this invention is an amount sufficient to impart the desirable effects known to be produced by cellulase on cellulose containing fabrics. Preferably, the cellulase in the detergent composition is employed in a concentration of about 10 ppm to about 20,000 ppm of detergent.

The specific concentration of cellulase enzyme employed in the detergent composition is preferably selected so that upon dilution into a wash medium, the concentration of cellulase enzyme is in a range of about 0.01 to about 1000 ppm, preferably from about 0.02 ppm to about 500 ppm, and most preferably from about 0.5 ppm to about 250 ppm total protein. The specific amount of cellulase enzyme employed in the detergent composition will depend on the extent to which the detergent will be diluted upon addition to water so as to form a wash solution.

The detergent compositions of the present invention may be in any art recognized form, for example, as a liquid diluent, in granules, in emulsions, in gels, or in pastes. Such forms are well known to the skilled artisan. When a solid detergent composition is employed, the cellulase is preferably formulated as granules. Preferably, the granules can be formulated so as to additionally contain a cellulase protecting agent. See, for instance, U.S. Ser. No. 07/642,669 filed Jan. 17, 1991 as Attorney Docket No. 010055-073 and entitled "GRANULES CONTAINING BOTH AN ENZYME AND AN ENZYME PROTECTING AGENT AND DETERGENT COMPOSITIONS CONTAINING SUCH GRANULES" which application is incorporated herein by reference in its entirety. Likewise, the granule can be formulated so as to contain materials to reduce the rate of dissolution of the granule into the wash medium. Such materials and granules are disclosed in U.S. Pat. No. 5,254,283 which is incorporated herein by reference in its entirety.

The detergent compositions of this invention employ a surface active agent, i.e., surfactant, including anionic, nonionic and ampholytic surfactants well known for their use in detergent compositions.

Suitable anionic surfactants for use in the detergent composition of this invention include linear or branched alkylbenzenesulfonates; alkyl or alkenyl ether sulfates having linear or branched alkyl groups or alkenyl groups; alkyl or alkenyl sulfates; olefinsulfonates; alkanesul-fonates and the like. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3.

Ampholytic surfactants include quaternary ammonium salt sulfonates, betaine-type ampholytic surfactants, and the like. Such ampholytic surfactants have both the positive and negative charged groups in the same molecule.

Nonionic surfactants generally comprise polyoxyalkylene ethers, as well as higher fatty acid alkanolamides or alkylene oxide adduct thereof, fatty acid glycerine monoesters, and the like.

Suitable surfactants for use in this invention are disclosed in British Patent Application No. 2 094 826 A, the disclosure of which is incorporated herein by reference.

Mixtures of such surfactants can also be used.

The surfactant or a mixture of surfactants is generally employed in the detergent compositions of this invention in an amount from about 1 weight percent to about 95 weight percent of the total detergent composition and preferably from about 5 weight percent to about 45 weight percent of the total detergent composition.

In addition to the cellulase composition and the surfactant (s), the detergent compositions of this invention can optionally contain one or more of the following components:

Hydrolases Except Cellulase

Such hydrolases include carboxylate ester hydrolase, thioester hydrolase, phosphate monoester hydrolase, and phosphate diester hydrolase which act on the ester bond; glycoside hydrolase which acts on glycosyl compounds; an enzyme that hydrolyzes N-glycosyl compounds; thioether hydrolase which acts on the ether bond; and a-amino-acyl-peptide hydrolase, peptidyl-amino acid hydrolase, acyl-amino acid hydrolase, dipeptide hydrolase, and peptidyl-peptide hydrolase which act on the peptide bond. Preferable among them are carboxylate ester hydrolase, glycoside hydrolase, and peptidyl-peptide hydrolase. Suitable hydrolases include (1) proteases belonging to peptidyl-peptide hydrolase such as pepsin, pepsin B, rennin, trypsin, chymotrypsin A, chymotrypsin B, elastase, enterokinase, cathepsin C, papain, chymopapain, ficin, thrombin, fibrinolysin, renin, subtilisin, aspergillopeptidase A, collagenase, clostridiopeptidase B, kallikrein, gastrisin, cathepsin D., bromelin, keratinase, chymotrypsin C, pepsin C, aspergillopeptidase B, urokinase, carboxypeptidase A and B, and aminopeptidase; (2) glycoside hydrolases (cellulase which is an essential ingredient is excluded from this group) α-amylase, β-amylase gluco amylase, invertase, lysozyme, pectinase, chitinase, and dextranse. Preferable among them are α-amylase and β-amylase. They function in acid to neutral systems, but one which is obtained from bacteria exhibits high activity in an alkaline system; (3) carboxylate ester hydrolase including carboxyl esterase, lipase, pectin esterase, and chlorophyllase. Especially effective among them is lipase.

The hydrolase other than cellulase is incorporated into the detergent composition as much as required according to the purpose. It should preferably be incorporated in an amount of 0.001 to 5 weight percent, and more preferably 0.02 to 3 weight percent, in terms of purified one. This enzyme should be used in the form of granules made of crude enzyme alone or in combination with other components in the detergent composition. Granules of crude enzyme are used in such an amount that the purified enzyme is 0.001 to 50 weight percent in the granules. The granules are used in an amount of 0.002 to 20 and preferably 0.1 to 10 weight percent. As with cellulases, these granules can be formulated so as to contain an enzyme protecting agent and a dissolution retardant material.

Cationic Surfactants and Long-Chain Fatty Acid Salts

Such cationic surfactants and long-chain fatty acid salts include saturated or unsaturated fatty acid salts, alkyl or alkenyl ether carboxylic acid salts, a-sulfofatty acid salts or esters, amino acid-type surfactants, phosphate ester surfactants, quaternary ammonium salts including those having 3 to 4 alkyl substituents and up to 1 phenyl substituted alkyl substituents. Suitable cationic surfactants and long-chain fatty acid salts are disclosed in British Patent Application No. 2 094 826 A, the disclosure of which is incorporated herein by reference. The composition may contain from about 1 to about 20 weight percent of such cationic surfactants and long-chain fatty acid salts.

Builders

A. Divalent Sequestering Agents.

The composition may contain from about 0 to about 50 weight percent of one or more builder components selected from the group consisting of alkali metal salts and alkanolamine salts of the following compounds: phosphates, phosphonates, phosphonocarboxylates, salts of amino acids, aminopolyacetates high molecular electrolytes, non-dissociating polymers, salts of dicarboxylic acids, and aluminosilicate salts. Suitable divalent sequestering agents are disclosed in British Patent Application No. 2 094 826 A, the disclosure of which is incorporated herein by reference.

B. Alkalis or Inorganic Electrolytes

The composition may contain from about 1 to about 50 weight percent, preferably from about 5 to about 30 weight percent, based on the composition of one or more alkali metal salts of the following compounds as the alkalis or inorganic electrolytes: silicates, carbonates and sulfates as well as organic alkalis such as triethanolamine, diethanolamine, monoethanolamine and triisopropanolamine.

Antiredeposition Agents

The composition may contain from about 0.1 to about 5 weight percent of one or more of the following compounds as antiredeposition agents: polyethylene glycol, polyvinyl alcohol, polyvinylpyrrolidone and carboxymethylcellulose.

Among them, a combination of carboxymethyl-cellulose and/or polyethylene glycol with the cellulase composition of the present invention provides for an especially useful dirt removing composition.

Bleaching Agents

The use of the cellulase of the present invention in combination with a bleaching agent such as sodium percarbonate, sodium perborate, sodium sulfate/hydrogen peroxide adduct and sodium chloride/hydrogen peroxide adduct or/and a photo-sensitive bleaching dye such as zinc or aluminum salt of sulfonated phthalocyanine further improves the detergenting effects.

Bluing Agents and Fluorescent Dyes

Various bluing agents and fluorescent dyes may be incorporated in the composition, if necessary. Suitable bluing agents and fluorescent dyes are disclosed in British Patent Application No. 2 094 826 A, the disclosure of which is incorporated herein by reference.

Caking Inhibitors

The following caking inhibitors may be incorporated in the powdery detergent: p-toluenesulfonic acid salts, xylene-sulfonic acid salts, acetic acid salts, sulfosuccinic acid salts, talc, finely pulverized silica, clay, calcium silicate (such as Micro-Cell of Johns Manville Co.), calcium carbonate and magnesium oxide.

Masking Agents for Factors Inhibiting the Cellulase Activity

The cellulase composition of this invention are deactivated in some cases in the presence of copper, zinc, chromium, mercury, lead, manganese or silver ions or their compounds. Various metal chelating agents and metal-precipitating agents are effective against these inhibitors.

They include, for example, divalent metal ion sequestering agents as listed in the above item with reference to optional additives as well as magnesium silicate and magnesium sulfate.

Cellobiose, glucose and gluconolactone act sometimes as the inhibitors. It is preferred to avoid the co-presence of these saccharides with the cellulase as far as possible. In case the co-presence in unavoidable, it is necessary to avoid the direct contact of the saccharides with the cellulase by, for example, coating them.

Long-chain-fatty acid salts and cationic surfactants act as the inhibitors in some cases. However, the co-presence of these substances with the cellulase is allowable if the direct contact of them is prevented by some means such as tableting or coating.

The above-mentioned masking agents and methods may be employed, if necessary, in the present invention.

Cellulase-Activators

The activators vary depending on variety of the cellulases. In the presence of proteins, cobalt and its salts, magnesium and its salts, and calcium and its salts, potassium and its salts, sodium and its salts or monosac-charides such as mannose and xylose, the cellulases are activated and their deterging powers are improved remarkably.

Antioxidants

The antioxidants include, for example, tert-butyl-hydroxytoluene, 4,4'-butylidenebis(6-tert-butyl-3-methylphenol), 2,2'-butylidenebis(6-tert-butyl-4-methylphenol), monostyrenated cresol, distyrenated cresol, monostyrenated phenol, distyrenated phenol and 1,1-bis(4-hydroxy-phenyl)cyclohexane.

Solubilizers

The solubilizers include, for example, lower alcohols such as ethanol, benzenesulfonate salts, lower alkylbenzene-sulfonate salts such as p-toluenesulfonate salts, glycols such as propylene glycol, acetylbenzene-sulfonate salts, acetamides, pyridinedicarboxylic acid amides, benzoate salts and urea.

The detergent composition of the present invention can be used in a broad pH range of from acidic to alkaline pH. In a preferred embodiment, the detergent composition of the present invention can be used in mildly acidic, neutral or alkaline detergent wash media having a pH of from above 5 to no more than about 11.

Aside from the above ingredients, perfumes, buffers, preservatives, dyes and the like can be used, if desired, with the detergent compositions of this invention. Such components are conventionally employed in amounts heretofore used in the art.

When a detergent base used in the present invention is in the form of a powder, it may be one which is prepared by any known preparation methods including a spray-drying method and a granulation method. The detergent base obtained particularly by the spray-drying method and/or spray-drying granulation method are preferred. The detergent base obtained by the spray-drying method is not restricted with respect to preparation conditions. The detergent base obtained by the spray-drying method is hollow granules which are obtained by spraying an aqueous slurry of heat-resistant ingredients, such as surface active agents and builders, into a hot space. After the spray-drying, perfumes, enzymes, bleaching agents, inorganic alkaline builders may be added. With a highly dense, granular detergent base obtained such as by the spray-drying-granulation method, various ingredients may also be added after the preparation of the base.

When the detergent base is a liquid, it may be either a homogeneous solution or an inhomogeneous dispersion. For removing the decomposition of carboxymethylcellulose by the cellulase in the detergent, it is desirable that carboxymethylcellulose is granulated or coated before the incorporation in the composition.

The detergent compositions of this invention may be incubated with cellulose containing fabric, for example soiled fabrics, in industrial and household uses at temperatures, reaction times and liquor ratios conventionally employed in these environments. The incubation conditions, i.e., the conditions effective for treating cellulose containing fabrics with detergent compositions according to the present invention, will be readily ascertainable by those of skill in the art. Accordingly, the appropriate conditions effective for treatment with the present detergents will correspond to those using similar detergent compositions which include wild-type cellulase.

As indicated above, detergents according to the present invention may additionally be formulated as a pre-wash in the appropriate solution at an intermediate pH where sufficient activity exists to provide desired improvements softening, depilling, pilling prevention, surface fiber removal or cleaning. When the detergent composition is a pre-soak (e.g., pre-wash or pre-treatment) composition, either as a liquid, spray, gel or paste composition, the cellulase enzyme is generally employed from about 0.0001 to about 1 weight percent based on the total weight of the pre-soak or pre-treatment composition. In such compositions, a surfactant may optionally be employed and when employed, is generally present at a concentration of from about 0.005 to about 20 weight percent based on the total weight of the pre-soak. The remainder of the composition comprises conventional components used in the pre-soak, i.e., diluent, buffers, other enzymes (proteases), and the like at their conventional concentrations.

Also, it is contemplated that compositions comprising cellulase enzymes described herein can be used in home use as a stand alone composition suitable for restoring color to faded fabrics (see, for example, U.S. Pat. No. 4,738,682, which is incorporated herein by reference in its entirety) as well as used in a spot-remover.

The use of the cellulase according to the invention may also be particularly effective in feed additives and in the processing of pulp and paper. These additional industrial applications are described in, for example, PCT Publication No. 95/16360 and Finnish Granted Patent No. 87372, respectively.

In order to further illustrate the present invention and advantages thereof, the following specific examples are given with the understanding that they are being offered to illustrate the present invention and should not be construed in any way as limiting its scope.

EXAMPLES

Example 1

Production and Purification of EGVI

A strain of *Trichoderma longibrachiatum* which was genetically manipulated to be unable to produce CBHI, CBHII, EGI, EGII and EGIII was made according to known methods for producing such deleted strains and fermented under conditions to induce cellulase production (see, for example, the methods provided in U.S. Pat. Nos. 5,328,841, 5,472,864 and 5,475,101). Purification followed a two-stage column purification as follows:

First Column: Mono-Q (Pharmacia HR 5/5, 5×50 mm, 1 mL Bed Volume)

Buffer A: 10 mM Histidine, pH 6.0

Buffer B: 10 mM Histidine, pH 6.0+1.0 M NaCl

Flow rate: 1 mL/min
Gradient: 0–40% B in 20 min

1. UF concentrate (1 mL) at 5 mg/ml protein was desalted on a NAP-10 column (Pharmacia) equilibrated with buffer A. The final volume was 1.5 mL.
2. The entire sample (5 mg) was loaded on a Mono-Q column equilibrated with buffer A.
3. After the flow-through material had eluted, the gradient was started.
4. Material containing EGVI eluted at ~25% buffer B and was collected.

Second Column: Mono-S (Pharmacia HR 5/5, 5×50 mm, 1 mL Bed Volume)
Buffer A: 10 mM Sodium Acetate, pH 5.0
Buffer B: 10 mM Sodium Acetate, pH 5.0+1.0 M NaCl
Flow rate: 1 mL/min
Gradient: 0–40% B in 20 min 1. The eluate from the Mono-Q column was desalted on a PD-10 column (Pharmacia) equilibrated with buffer A. The final volume was 3.5 mL.
2. The entire sample (~2 mg) was loaded on a Mono-S column equilibrated with buffer A.
3. After the flow-through material had eluted, the gradient was started. EGVI eluted at ~15% buffer B and was collected.

Example 2
Characteristics of Purified EGVI

Figure 3:
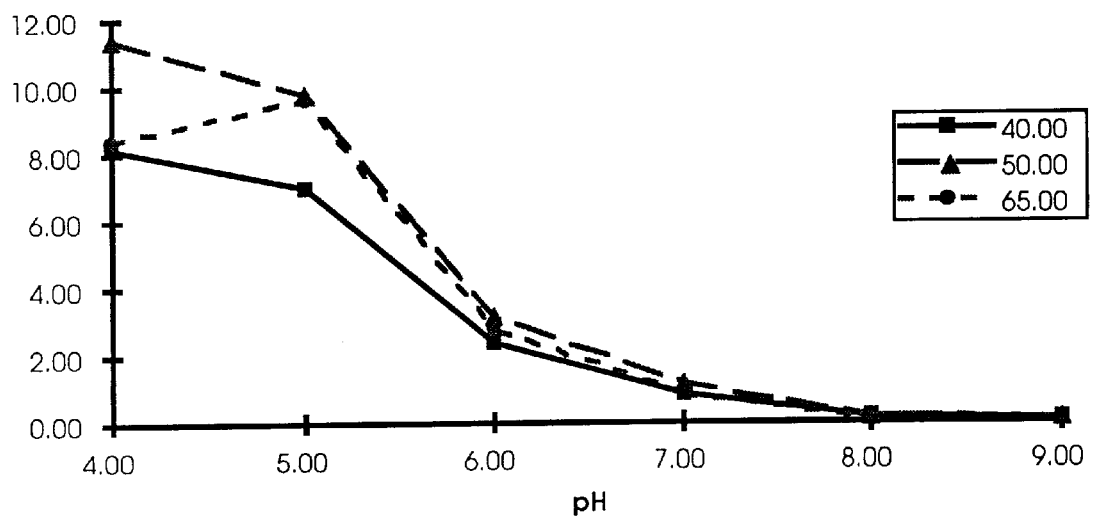
FIG. 3 illustrates the activity of EGVI on RBB-CMC at varying pH and temperature.

The specific activity of EGVI was measured at pH 4, 5, 6, 7, 8 and 9 at 40° C., 50° C. and 65° C. as follows. 5 to 20 µl of enzyme solution was added at a concentration sufficient to provide the requisite amount of enzyme in the final solution. 250 µl of 2 weight percent RBB-CMC (Remazol Brilliant Blue R-Carboxymethylcellulose—commercially available from MegaZyme, 6 Altona Place, North Rocks, N.S.W. 2151, Australia) was added to 0.05M citrate/phosphate buffer at pH 4, 5, 6, 7, 8 and 9. The composition was vortexed and incubated at 40° C., 50° C. or 60° C. for 30 minutes and then chilled in an ice bath for 5–10 minutes. 1000 µl of ethanol containing 0.3M sodium acetate and 0.02M zinc acetate were added, the mixture centrifuged and the supernatant poured into cuvettes. The optical density was measured at 590 nm. Higher levels of optical density correspond to higher levels of enzyme activity. The results are provided in FIG. 3.

Figure 2:
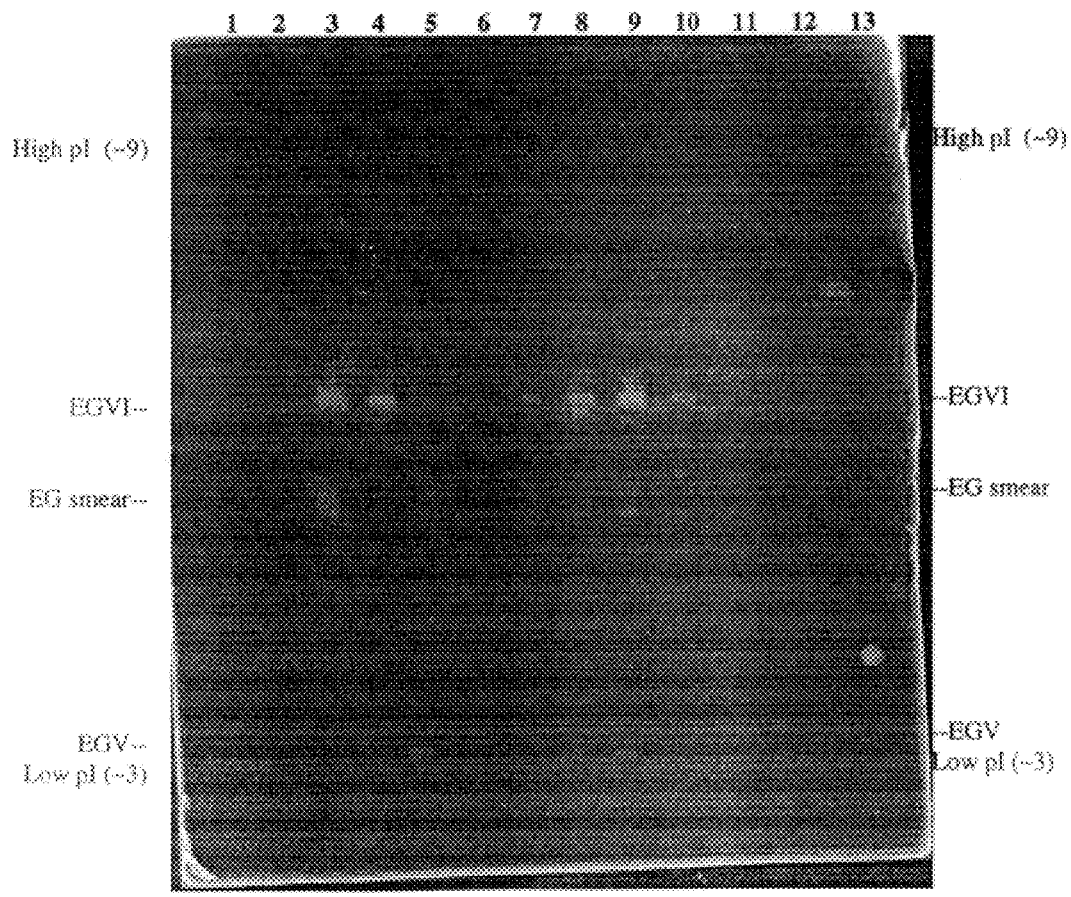
FIG. 2 illustrates an activity overlay of an isoelectric focusing gel illustrating activity on RBB-CMC of EGVI.

As shown in FIG. 2, EGVI shows an activity optimum at pH 5 at 65° C. whereas the activity peak is at lower pH at lower temperatures, illustrating a generally acidic pH optimum below pH 4.

The molecular weight of EGVI was measured by SDS-PAGE to be approximately 100 kD and the pI estimated from IEF gels was about 6.2. An RBB-CMC overlay was placed on the IEF gel to confirm the presence of celluloytic activity. The results are shown in FIG. 2. As shown in FIG. 2, the bands corresponding to EGVI distinctly showed cellulolytic activity.

Example 3
Determination of Cellulose Binding by EGVI

EGVI was tested for its ability to bind to cellulose based compounds by incubating a sample containing EGVI with a solid cellulosic substrate for a given period of time and analyzing the supernatant for the disappearance of EGVI through IEF gel electrophoresis. EGVI containing UF concentrated broth was prepared by first desalting into a 10 mM Na Acetate buffer (pH 5) to a concentration of 2.5 mg/ml total protein. One milliliter of the enzyme solution was added to 250 mg of various cellulose samples. These samples were then mixed for one hour. The samples were then centrifuged and the supernatant collected for IEF gel analysis. The absence of EGVI in the sample, as determined by the disappearance of the EGVI band, would implicate cellulose binding by EGVI. Performance of this assay indicated cellulose binding by EGVI with the following substrates: Avicel (FMC Type pH-101); and Sigma Type 50, Type 101, Type 101F and alpha cellulose (Cat # S-5504, S-6790, S-6195, C-8002). Accordingly, the conclusion follows that EGVI possesses cellulose binding activity.

We claim:

1. A purified cellulase composition, said purified cellulase composition corresponding to a naturally occurring cellulase produced during a fermentation of *Trichoderma longibrachiatum* which exhibits a molecular weight of about 95–105 kD as measured on SDS-PAGE gel and a pI of about 5.6–6.8 as measured on an IEF gel.

2. The purified cellulase composition according to claim 1, wherein said cellulase has optimum activity at pH 5 at 65° C. and pH 4 or lower at 50° C. and 40° C.

3. The purified cellulase composition according to claim 1, wherein said purified cellulase is produced by Trichoderma sp.

4. The purified cellulase composition according to claim 3, wherein said cellulase is produced by *Trichoderma longibrachiatum*.

5. A method for preparing a purified cellulase composition comprising the steps of:
   (a) preparing a fermentation culture of a microorganism which produces a cellulase composition corresponding to a naturally occurring cellulase produced during a fermentation of *Trichoderma longibrachiatum* which exhibits a molecular weight of about 95–105 kD as measured on SDS-PAGE gel and a pI of about 5.6–6.8 as measured on an IEF gel; and
   (b) separating said cellulase from said microorganisms to form a purified cellulase composition.

6. The method according to claim 5, wherein said microorganism is a fungus.

7. The method according to claim 6, wherein said fungus is a filamentous fungus.

8. The method according to claim 7, wherein said filamentous fungus is Trichoderma spp.

9. The method according to claim 8, wherein said Trichoderma spp. is *Trichoderma longibrachiatum*.

10. The method according to claim 8, wherein said Trichoderma spp. is genetically manipulated so as to be unable to produce cellulases corresponding to CBHI, CBHII, EGI, EGII or EGIII in *Trichoderma longibrachiatum*.

11. A detergent composition comprising a purified cellulase composition, said purified cellulase composition corresponding to a naturally occurring cellulase produced during a fermentation of *Trichoderma longibrachiatum* which exhibits a molecular weight of about 95–105 kD as measured on SDS-PAGE gel and a pI of about 5.6–6.8 as measured on an IEF gel.

12. The detergent composition according to claim 11, wherein said purified cellulase is produced by *Trichoderma longibrachiatum*.

13. A stonewashing composition comprising a purified cellulase composition, said purified cellulase composition corresponding to a naturally occurring cellulase produced during a fermentation of *Trichoderma longibrachiatum* which exhibits a molecular weight of about 95–105 kD as measured on SDS-PAGE gel and a pI of about 5.6–6.8 as measured on an IEF gel.

14. The stonewashing composition according to claim 13, wherein said purified cellulase is produced by *Trichoderma longibrachiatum*.

15. An animal feed additive comprising a purified cellulase composition, said purified cellulase composition corresponding to a naturally occurring cellulase produced during a fermentation of *Trichoderma longibrachiatum* which exhibits a molecular weight of about 95–105 kD as measured on SDS-PAGE gel and a pI of about 5.6–6.8 as measured on an IEF gel.

16. A method for treating a cellulose containing fabric comprising the steps of:
    (a) preparing an aqueous solution comprising a purified cellulase composition, said purified cellulase composition corresponding to a naturally occurring cellulase produced during a fermentation of *Trichoderma longibrachiatum* which exhibits a molecular weight of about 95–105 kD as measured on SDS-PAGE gel, a pI of about 5.6–6.8 as measured on an IEF gel;
    (b) contacting said cellulose containing fabric with said aqueous solution.

17. The method according to claim 16, wherein said treating comprises stonewashing of cotton-containing indigo-dyed denim.

18. A method for treating wood pulp comprising contacting said wood pulp with an aqueous solution comprising a purified cellulase composition, said purified cellulase composition corresponding to a naturally occurring cellulase produced during a fermentation of *Trichoderma longibrachiatum* which exhibits a molecular weight of about 95–105 kD as measured on SDS-PAGE gel and a pI of about 5.6–6.8 as measured on an IEF gel.

19. A method for treating grain during the processing of starch comprising contacting said grain with a purified cellulase composition, said purified cellulase composition corresponding to a naturally occurring cellulase produced during a fermentation of *Trichoderma longibrachiatum* which exhibits a molecular weight of about 95–105 kD as measured on SDS-PAGE gel and a pI of about 5.6–6.8 as measured on an IEF gel.

* * * * *